United States Patent [19]

Rindt et al.

[11] Patent Number: 5,151,367
[45] Date of Patent: Sep. 29, 1992

[54] DETECTOR FOR ENZYMATICALLY DETERMINING GAS SAMPLES

[75] Inventors: Klaus-Peter Rindt; Stephan Scholtissek, both of Lübeck, Fed. Rep. of Germany

[73] Assignee: Drägerwerk Aktiengesellschaft, Lübeck, Fed. Rep. of Germany

[21] Appl. No.: 577,540

[22] Filed: Sep. 5, 1990

[30] Foreign Application Priority Data

Sep. 6, 1989 [DE] Fed. Rep. of Germany ....... 3929541

[51] Int. Cl.⁵ ............................................. G01N 21/75
[52] U.S. Cl. .................................... 435/288; 436/167; 436/169; 422/56; 435/807
[58] Field of Search ............... 435/288, 291, 817, 807, 435/296, 31, 288; 204/403; 422/56, 58, 101; 436/169, 167, 181

[56] References Cited

U.S. PATENT DOCUMENTS

| | | | |
|---|---|---|---|
| 4,416,984 | 11/1983 | Wheeler, Jr. | 435/296 |
| 4,741,437 | 5/1988 | Gorski et al. | 435/31 |
| 4,761,379 | 8/1988 | Williams et al. | 435/296 |
| 4,956,275 | 9/1988 | Zuk et al. | 435/288 |
| 5,013,668 | 5/1991 | Fields | 435/807 |

Primary Examiner—James C. Housel
Assistant Examiner—Lien Tran
Attorney, Agent, or Firm—Walter Ottesen

[57] ABSTRACT

A detector for enzymatically determining components in gases and aerosols and includes a porous filter disposed in a housing. The filler absorbs the aqueous reagent solution, the substrates and the enzymes and is brought into communication with a sample to be investigated. The detector of the invention is improved in that a separate preparation of the components needed for the detection takes place in the housing itself. The components combine without additional ancillary equipment or manual movements. The components are combined in that a porous filler is accommodated in a holder and is tightly held thereagainst and a filler tip projects outwardly therefrom. The filler tip is dipped in a supply vessel containing the reagent solution. A penetratable cover membrane which is impermeable to water is arranged between the filler tip and the supply vessel.

23 Claims, 1 Drawing Sheet

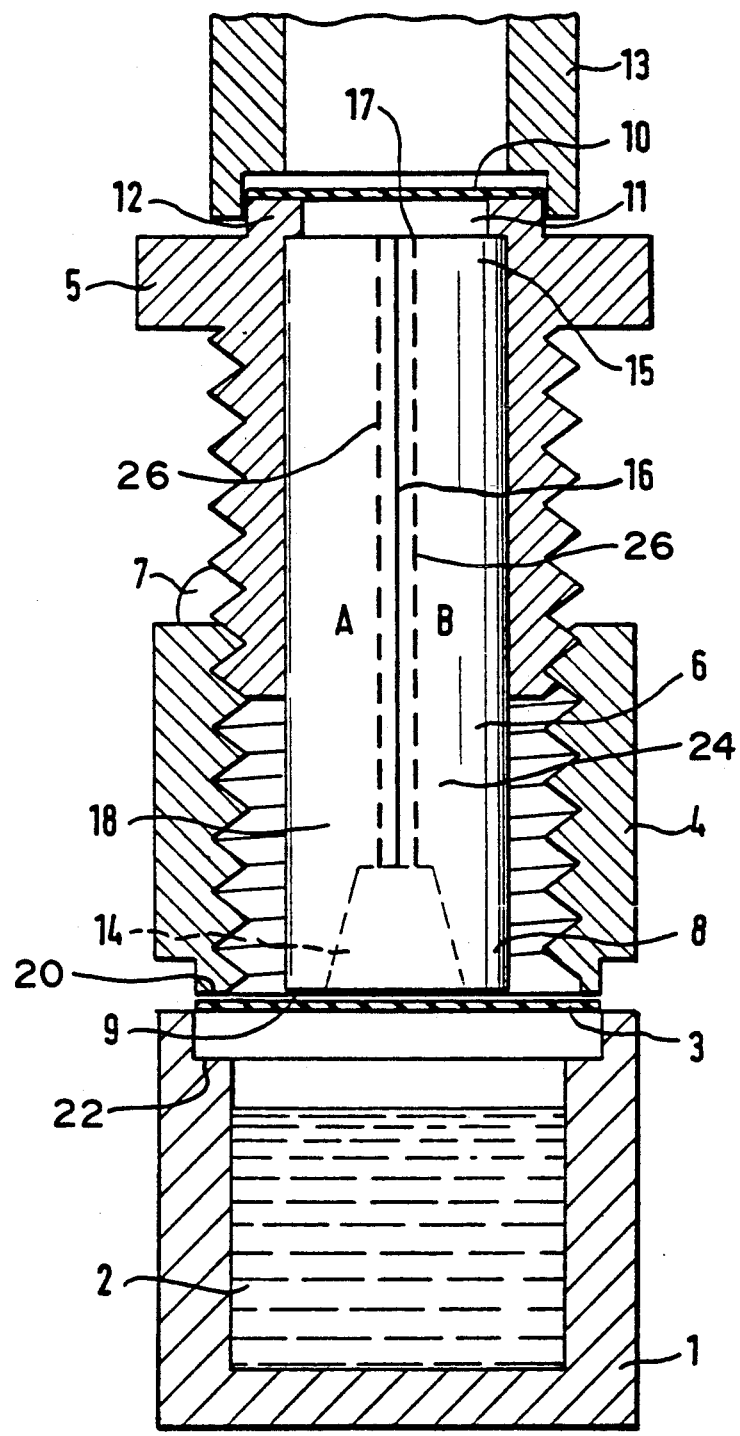

DETECTOR FOR ENZYMATICALLY DETERMINING GAS SAMPLES

FIELD OF THE INVENTION

The invention relates to a detector for the enzymatic determination of components in gases and aerosols and includes a porous filler disposed in a housing. The filler accommodates the aqueous reagent solution, the substrate and the enzymes. The housing has at least one opening by means of which the filler is in detecting contact with the air sample.

BACKGROUND OF THE INVENTION

A detector of the kind described above is disclosed in U.S. patent application Ser. No. 208,678, now abandoned, having the title "Method for Detecting Gaseous Materials by Means of an Enzymatic Redox Reaction and Apparatus therefor" filed on Jun. 20, 1988 and incorporated herein by reference.

This detector includes a porous filler disposed in a tubular vessel open at both ends. The filler comprises a carrier material on which the enzyme is applied for example by means of freeze drying or the carrier material can first be completely uncharged. The detector is closed in its operational ready condition. To prepare for measurement, the detector is opened and the carrier material is impregnated with a reagent solution. If the carrier material already contains the enzyme, then the reagent solution comprises, for example, an electron acceptor/donator complex and a chromogen which makes possible a color reaction required for the detection or, for the case wherein the carrier material is completely uncharged, the reagent solution at the same time contains the enzyme necessary for the detection. In both cases, the reagent solution must be separately prepared for each measurement so that the reagent solution can be directly applied to the filler in advance of the air sample determination.

It is also possible to separately store a completely prepared reagent solution; however, the handling and most importantly, the preparation of the necessary supplies is complex. The preparation to determine the gas specimen requires experienced manual operations by the user which must be carried out without error for a successful determination. Furthermore, the user must initially be able to estimate which quantities of components are to be provided in the reagent solution so that the anticipated quantity of the gas components to be determined can be completely converted. Since this cannot always be determined in advance, control or limiting measurements are necessary in accordance with measurement results.

SUMMARY OF THE INVENTION

It is an object of the invention to improve upon a detector of the kind described above so that the separate preparation of the components required for the detection takes place in the housing itself with the components combining without additional ancillary means or manipulations.

According to a feature of the invention, the porous filler is accommodated in a holder and is held in tight engagement therewith. A tip of the filler projects from this holder and can be dipped or partially immersed in a reagent solution contained in a supply vessel. A penetrable cover membrane which is impermeable to water is arranged between the filler tip and the supply vessel.

The advantage of the invention is essentially seen in that the components necessary for a previously determined detection area are available in the detector itself and are combined with the filler in the measurement ready condition only directly ahead of carrying out the determination of the gas sample. The detector prepared in this manner is in some measure inactive in the operational ready condition and is activated by simply bringing together the filler and the reagent solution for the measurement with no additional chemical preparations being required.

To carry out the measurement sequence, a series of detectors can be made ready which are sensitive to different concentrations of the gas component to be detected. In this way, the manipulation is reliable and can be easily carried out even by inexperienced users. The filler becomes filled by suction after dipping the filler tip into the reagent solution. The component to be detected reaches the filler by diffusion and is there specifically converted by the enzyme.

In a color reaction which takes place thereafter, a colorant in the solution is formed of such a color intensity which is directly proportional to the concentration of the component to be detected. Therefore, a colorization zone of a specific color intensity is determinable as a measuring result on the surface of the filler subjected to the air sample. The reaction partners are supplied continuously from the supply vessel so that the coloration zone remains on the filler surface being observed with the coloration zone becoming ever deeper with advancing measurement duration.

The evaluation can take place with simply the eye by making a color comparison with calibrated color standards as well as reflectrometrically. The enzyme determining the specificity of the reaction can either be dissolved in the reagent solution or be present in a bond on the porous filler.

The cover membrane can advantageously be configured as a closure for the supply vessel. In this way, it is possible to maintain the supply vessel filled with the reagent solution in an undisturbed manner over a longer period of time. The cover membrane is only penetrated when bringing together the filler tip and the supply vessel. The cover membrane can either be welded to the edge of the supply vessel or be clamped by means of a clamping ring in a corresponding annular slot of the vessel wall.

If for example, a decreased long-term stability of the reagent solution requires a filling of the supply vessel directly in advance of the measurement, then it is advantageous to provide the cover membrane as a covering for the filler tip projecting out of the holder. The membrane is penetrated by a limited thrust of the filler tip out of the holder so that the reagent solution can be drawn up by suction when the tip is thereafter dipped into the filled supply vessel. The membrane can here too be welded to the sleeve edge or be held by means of a clamping ring.

It is advantageous to provide an upper vessel part at the supply vessel to ensure a reliable introduction of the filler tip into the supply vessel. The vessel upper part can be a threaded piece into which the holder threadably engages.

It is also advantageous to configure the upper vessel part as an adaptor sleeve into which the holder is insertable in a seal-tight manner. In both cases, the assurance is provided that the filler tip absorbs the entire supply of reagent solution and that no liquid exits on the side walls between the filler tip and the inside wall of the vessel during the introduction which otherwise would be lost with respect to the determination. The embodiment of the vessel upper part as a threaded piece affords the advantage that the filler tip is introduced in a controlled manner and that the thrust is predeterminable by the winding pitch and the number of turns.

It is advantageous to configure the filler tip with at least one compensating bore projecting into the filler to facilitate a rapid insertion of the filler tip for a vessel upper part configured as an adaptor sleeve. Now the filler can be rapidly dipped into the supply vessel without pressing liquid out between the filler and the inner wall of the supply vessel as a consequence of a rapid displacement of the reagent solution. A large portion of the reagent solution is first pressed into the compensating bore during pressing from which the solution can distribute itself uniformly in the filler when pressing is completed.

The membrane for closing the supply vessel can be glued into the latter or welded thereto. However, it is advantageous to configure the vessel upper part as a clamping sleeve so that the membrane can be clamped between the supply vessel and the vessel upper part in a simple manner and thereby prevent the reagent solution from flowing out of the vessel.

It is advantageous to provide the filler tip with a cutting surface to ensure a reliable penetration of the membrane. This cutting surface can comprise a tip which expands conically toward the filler. The cutting surface can also be granular glass applied separately on the filler. It has been shown to be especially advantageous however to configure the filler as a glass sinter body. In this way, adequate porosity is assured on the one hand while, on the other hand, the glass sinter filler tip has cutting characteristics for the membrane whereby it simultaneously acts as a cutting surface.

If it is intended to conduct a long-term dosimetry with the detector, then the access of the components to be detected must take place in a controlled manner. This can be realized, for example, by means of a closure of the opening of the filler to the ambient by means of a diffusion membrane or by means of a diffusion attachment configured as a tube or also by means of a combination of both measures.

A diffusion attachment also contributes to quieting the diffusion. The diffusion attachment can be configured as a single piece with the holder or it can be mounted on the holder by means of a clamping attachment. The diffusion attachment can either be mounted in lieu of a diffusion membrane or, as an addition to this membrane.

In order to be able to simultaneously detect either two or more gas components or to conduct a reference measurement, it is advantageous to partition the filler in its longitudinal direction between the filler tip and the opening and to connect the component fillers at their partition surfaces with a foil impermeable to the reagent solution and the components to be detected. The component bodies are charged with various enzymes for simultaneously determining several gaseous components. These enzymes are capable of different reactions with the gas components which are sensitive therefor. On the other hand, if it is intended to simultaneously carry out a reference measurement, one of the component bodies is provided with an enzyme while the other is not so that only that component is colored which is provided with the enzyme.

To improve the storage capability, it is recommended that the holder as well as the supply vessel and the vessel upper part be made out of a light-impermeable material in order to make possible the use of light-sensitive substances. A guide stop can be provided as a further improvement to ensure a reliable manipulation. This guide stop must be overcome in order to dip the filler into the reagent solution. This stop can for example be configured as a cam-shape riser on the vessel upper part and forms a resistance when dipping the holder into the supply vessel and must be deliberately passed. The cam is broken by this action. If the filler tip is covered with a cover membrane, then this is simultaneously penetrated.

BRIEF DESCRIPTION OF THE DRAWING

The invention will now be described with reference to the drawing wherein the single FIGURE is a section view taken through a detector according to the invention.

DESCRIPTION OF THE PREFERRED EMBODIMENTS OF THE INVENTION

The detector shown in the drawing includes a supply vessel 1 having a reagent solution 2 disposed therein. The supply vessel is closed off with a water-impermeable cover membrane 3. A vessel upper part 4 is snapped onto the supply vessel 1 which clamps the edge of the membrane 3 into its position in a seal-tight manner. More specifically, the membrane 3 can be clamped between clamping surface 20 formed on the vessel upper part 4 and a clamping surface 22 formed as an annular step in the supply vessel 1. The clamping surfaces (20, 22) then conjointly define a clamping interface for clamping the cover membrane 3 in position as a closure of the supply vessel. The vessel upper part has an internal thread into which a holder 5 or a porous fill body or tiller 6 threadably engages up to a cam-shaped stop 7. The cam-shaped stop 7 is broken and overridden when the holder 5 is rotated in the vessel upper part 4 to move the filler 6 downwardly so that its lower end portion 24 is dipped into the reagent solution 2. The filler 6 projects with the lower end portion 24, which includes a filler tip 8 out of the holder 5 and extends with its end having a cutting surface 9 up to almost the cover membrane 3. The filler is subdivided into two component regions (A, B) which conjointly define a partition interface 26 and are connected by a partition foil 16. Only the component region A contains the enzyme required for the detecting reaction.

The holder 5 has an opening 11 facing toward the ambient. The opening 11 is provided with a diffusion membrane 10 permeable for the gas component to be detected. The opening 11 includes a collar 12 onto which a diffusion attachment 13 detents. The diffusion attachment 13 acts as a diffusion length. The filler tip 8 contains a compensating bore 14 extending into the filler 6.

The reagent solution 2 is completely absorbed by the porous filler 6. The substrate is lyophilized in the lower region 18 of the filler and the enzyme is lyophilized in its upper region 15. The substrate and enzyme are dissolved in the reagent solution along the path to the surface 17 of the porous filler 6 subjected to the air sample and are brought to the surface 17. After this activation, the component to be detected reaches the surface 17 subjected to the ambient via the diffusion membrane 10. The specific conversion of the component by the enzyme causes the development of the colorant present in the reagent solution in a color reaction which then takes place. The color intensity is directly proportional to the concentration of the component to be detected and is used for evaluation.

A liquid transport from the supply vessel 1 to the surface 17 takes place by means of the vaporization of the water of the reagent solution 2 at the surface 17 of the porous filler 6. The reagents, substrates and enzymes are concentrated at the surface 17 by this transport. At the same time, the diffusion of the formed colorant away from the surface 17 into the filler 6 is prevented so that no colorant for the evaluation is lost. Since only component A of the two components (A, B) contains the enzyme necessary for the detection, the color reaction takes place only on component A. The partition foil 16 is impermeable for the reagent solution and the component to be detected so that a clean separation between the color reaction on component A from the uncolored component B is distinguishable.

Examples for enzymatically determining components in gases and aerosols are given in copending U.S. application Ser. No. 448,235 entitled "Enzymatic Detection Device for detecting a Gaseous or Aerosol Substance" filed on Dec. 11, 1989 and incorporated herein by reference.

Hydrogen peroxide, for example, can be detected in the manner described below.

For detecting, for example, hydrogen peroxide as the reactant for the enzyme horseradish peroxidase, a solution of 1 mMol/l 4-aminoantipyrine and 1 mMol/l of N-ethyl-N-sulphopropyl-m-toluidine is prepared in a 50 mMol/l phosphate buffer as coloring reagents. The phosphate buffer is intended to guarantee a pH-value of 7.3. With this type of formulation, hydrogen peroxide is selectively detectable via the peroxidase (POD) as a biocatalyst by means of the color reaction. The chromogens are formed by aminoantipyrine and ethyl-sulphopropyltoluidine and these chromogens combine to a coloring substance because of the enzyme reaction.

The detection of hydrogen peroxide with a chromogen as a coloring reagent, which is directly converted into a coloring substance because of the enzyme reaction, occurs by means of a solution which contains two international units of the enzyme horseradish peroxidase (POD) as well as a coloring reagent in the form of a millimolar 2.2' acino-bis-(3-ethylbenzthiazoline-6-sulphonic acid) in a 0.1 molar TRIS-HCl-buffer pH 8.0.

For the long-term measurement of hydrogen peroxide, a less sensitive coloring system is used such as a solution of 1 mMol/l 4-chlorine-1-naphthol in 50 mMol/l TRIS-HCl and 0.2 Mol/l sodium chloride solution.

It is understood that the foregoing description is that of the preferred embodiments of the invention and that various changes and modifications may be made thereto without departing from the spirit and scope of the invention as defined in the appended claims.

What is claimed is:

1. A detector for enzymatically determining a component in a gas or aerosol sample, the detector comprising:
    an aqueous reagent solution;
    a supply vessel defining an interior for holding said aqueous reagent solution;
    a holder having a first opening;
    a filler for receiving a reagent and an enzyme;
    said enzyme being contained in at least one of said solution and said filler;
    said filler being disposed in said holder so as to be in tight contact engagement therewith, said filler having an upper portion defining an upper end face and a lower portion extending outwardly from said first opening;
    said holder having a second opening facing away from said first opening and communicating with said filler for permitting the component to be enzymatically detected to reach said upper end face of said upper portion;
    water-impermeable and penetrable membrane means for closing off said supply vessel and said reagent solution until said detector is ready for use;
    said membrane means being mounted between said lower portion of said filler and said supply vessel;
    displacement means for facilitating an advance of said filler from a first position wherein said filler is outside of said interior and a second position wherein said filler is moved into said interior to permit only said lower portion of said filler to be dipped into said solution thereby permitting said upper end face to remain exposed to the component to be detected;
    penetrating means for penetrating said membrane as said filler is advanced from said first position to said second position to allow said filler to enter said interior; and,
    said filler being porous to facilitate the liquid transport of said solution into and along said filler thereby bringing the reagent and enzyme to said upper end face where the enzyme enters into a reaction with the component to be detected acting as a substrate to the enzyme, and to build up a compound which reacts with the reagent to generate a color indication at said end face indicative of the concentration of the component in the sample.

2. The detector of claim 1, said membrane means being a cover membrane for closing said supply vessel.

3. The detector of claim 2, said cover membrane being mounted between said lower portion of said filler and said supply vessel so as to also close off said filler until said detector is ready for use.

4. The detector of claim 1, said displacement means including a vessel upper part interposed between said vessel and said holder for coacting with said holder for guiding said filler when advancing said filler from said first position to said second position for dipping said filler into said reagent solution.

5. The detector of claim 4, said holder and said vessel upper part conjointly defining an interface and said displacement means being a thread formed at said interface to permit said holder to be threadably displaced relative to said vessel upper part thereby advancing said filler from said first position to said second position.

6. The detector of claim 4, said vessel upper part being an adaptor sleeve for slideably receiving said holder in a seal-tight manner when said holder is inserted in said vessel upper part; and, said displacement means being a sliding interface conjointly defined by said adaptor sleeve and said holder for permitting said holder to slide relative to said adaptor sleeve to move said filler from said first position to said second position.

7. The detector of claim 1, said lower portion of said filler having a lower end face and defining at least one compensating bore extending into said filler at said lower end face.

8. The detector of claim 4, said membrane means being a cover membrane for closing said supply vessel; said vessel upper part and said supply vessel conjointly defining a clamping interface for clamping said cover membrane in position as a closure of said supply vessel.

9. The detector of claim 1, said lower portion of said filler having a lower end face; and, said penetrating means including a cutting surface formed on said lower end face for cutting through said membrane means as said filler is advanced from said first position to said second position.

10. The detector of claim 1, said filler being a glass sintered body.

11. The detector of claim 1, further comprising a diffusion membrane permeable to the component to be detected; and, means for holding said diffusion membrane in position for closing off said second opening.

12. The detector of claim 1, said holder having an end portion surrounding said second opening and said holder including a diffusion attachment mounted on said end portion in surrounding relationship to said second opening.

13. The detector of claim 4, said holder and said upper vessel part conjointly defining an interface whereat said holder can be moved relative to said upper vessel part to advance said filler toward the reagent solution; and, said displacement means further including an overridable guide stop arranged at said interface which is overridable to dip said lower end portion of said filler into said reagent solution.

14. The detector of claim 1 for detecting at least two components in the gas or aerosol sample, said filler being an elongated body extending along said holder and defining a longitudinal axis; said filler being partitioned into at least two component bodies in the direction of said axis; said two component bodies conjointly defining a partition interface; and, said detector further comprising a separation foil for connecting said two component bodies together at said partition interface; and, said separation foil being impermeable to said components contained in said sample.

15. The detector of claim 4, said holder, said supply vessel and said vessel upper part all being made of a light-impermeable material.

16. The detector of claim 1, said enzyme being contained in said solution.

17. The detector of claim 1, including means for lyophilizing an additional substrate in said lower portion of said filler.

18. The detector of claim 1, including means for lyophilizing said enzyme in said upper portion of said filler.

19. A detector for enzymatically determining a component in a gas or an aerosol sample, the detector comprising:
an aqueous reagent solution;
a supply vessel defining an interior for holding said aqueous solution containing a reagent;
said supply vessel having an upper end defining a vessel opening;
an annular member defining a longitudinal axis and being mounted on said upper end of said supply vessel;
a water-impermeable and penetrable membrane interposed between said annular member and said supply vessel for closing off said supply vessel and said aqueous solution until the detector is ready for use;
a holder having a first opening for receiving the component to be detected;
an elongated filler having a lower end portion and an upper end portion defining an upper end face, said filler being adapted to receive the reagent and an enzyme;
said enzyme being contained in at least one of said solution and said filler;
said filler being disposed in said holder so as to be tightly held thereby and so as to cause said upper end face to be exposed to the component to be detected through the first opening of the holder;
said holder having a second opening through which said lower end portion of said filler extends;
said holder being held in said annular member so as to be displaceable relative thereto along said axis and so as to cause said annular member to surround said lower end portion of said filler;
said holder and said filler being displaceable as a unit from a first position wherein said filler is outside of said interior to a second position wherein said filler is moved into said interior to permit only said lower portion of said filler to be dipped into said solution thereby permitting said upper end face to remain exposed to the component to be detected throughout the use of said detector;
penetrating means for penetrating said membrane as said holder and said filler are advanced from said first position to said second position thereby allowing said filler to enter said interior; and,
said filler being porous to facilitate the liquid transport of said solution into and along said filler thereby bringing the reagent and enzyme to said upper end face where the enzyme enters into a reaction with the component to be detected acting as a substrate to the enzyme, and to build up a compound which reacts with the reagent to generate a color indication at said end face indicative of the concentration of the component in the sample.

20. The detector of claim 19, said annular member having a longitudinal lower end, said longitudinal lower end and said upper end of said supply vessel conjointly defining a seal-tight interface to prevent any loss of said solution to the ambient environment after said membrane is penetrated.

21. The detector of claim 19, said enzyme being contained in said solution.

22. The detector of claim 19, including means for lyophilizing a further substrate in said lower portion of said filler.

23. The detector of claim 19, including means for lyophilizing said enzyme in said upper portion of said filler.

* * * * *

UNITED STATES PATENT AND TRADEMARK OFFICE
CERTIFICATE OF CORRECTION

PATENT NO. : 5,151,367
DATED : September 29, 1992
INVENTOR(S) : Klaus-Peter Rindt and Stephan Scholtissek It is certified that error appears in the above-identified patent and that said Letters Patent is hereby corrected as shown below:

In the Abstract, line 2: delete "filter" and substitute -- filler -- therefor.

In column 4, line 40: delete "tiller" and substitute -- filler -- therefor.

In column 4, line 46: after "tip 8", insert -- , --.

Signed and Sealed this

Nineteenth Day of October, 1993

Attest:

BRUCE LEHMAN

Attesting Officer     Commissioner of Patents and Trademarks